United States Patent [19]

Chow et al.

[11] Patent Number: 5,556,423
[45] Date of Patent: Sep. 17, 1996

[54] INDEPENDENT PHOTOELECTRIC ARTIFICIAL RETINA DEVICE AND METHOD OF USING SAME

[75] Inventors: Alan Y. Chow, Wheaton; Vincent Chow, Hanover Park, both of Ill.

[73] Assignee: Alan Y. Chow, Wheaton, Ill.

[21] Appl. No.: 230,504

[22] Filed: Apr. 20, 1994

Related U.S. Application Data

[63] Continuation-in-part of Ser. No. 56,672, May 3, 1993, Pat. No. 5,397,350.

[51] Int. Cl.$^6$ ........................................ A61N 1/05
[52] U.S. Cl. ........................... 607/54; 623/4; 623/24; 128/898; 607/116
[58] Field of Search ........................... 607/53, 54, 116, 607/141; 623/4, 5, 24; 128/898

[56] References Cited

U.S. PATENT DOCUMENTS

| | | |
|---|---|---|
| 2,760,483 | 10/1954 | Tassicker . |
| 3,594,823 | 7/1971 | Collins . |
| 3,628,193 | 12/1971 | Collins . |
| 3,766,311 | 10/1973 | Boll . |
| 3,848,608 | 11/1974 | Leonard . |
| 3,914,800 | 10/1975 | Collins . |
| 4,251,887 | 2/1981 | Anis . |
| 4,272,910 | 6/1981 | Danz . |
| 4,551,149 | 11/1985 | Sciarra .................................. 607/54 |
| 4,600,004 | 7/1986 | Lopez et al. . |
| 4,601,545 | 7/1986 | Kern . |
| 4,628,933 | 12/1986 | Michelson .............................. 623/4 |
| 4,750,498 | 6/1988 | Graham . |
| 4,836,202 | 6/1989 | Krasner . |
| 5,016,633 | 5/1991 | Chow ................................. 623/4 X |
| 5,024,223 | 6/1991 | Chow ................................. 623/4 X |
| 5,109,844 | 5/1992 | de Juan et al. ....................... 623/4 |

FOREIGN PATENT DOCUMENTS 0233789   8/1987   European Pat. Off. .

OTHER PUBLICATIONS

Exhibit A is an article published in *Science News*, Feb. 2, 1974, vol. 105, No. 5, p. 105.

(List continued on next page.)

*Primary Examiner*—William E. Kamm
*Assistant Examiner*—Jeffrey R. Jastrzab
*Attorney, Agent, or Firm*—Brinks Hofer Gilson & Lione

[57] ABSTRACT

Microscopic photodiode devices with semi-transparent surface electrodes are combined with a liquid or other suitable vehicle. Together they are injected into the subretinal space of the eye. The purpose of these microphotodiode photovoltaic devices is to transduce incident light into electric current which stimulate the overlying cellular layers of the retina. In persons suffering from visual dysfunction due to outer retinal layer damage, such devices may allow useful formed artificial vision. These independent surface electrode microphotodiodes (ISEMCPs) may be in the shape of microspheres, micro-cylinders or other micro-shapes. An off-center embedded ferromagnetic layer will confer magnetic susceptibility to the ISEMCPs. A magnetic field applied in the vicinity of the eye will align the ISEMCPs within the subretinal space directing their photoactive surface toward incident light. Alternatively ISEMCPs may be embedded, prealigned, in a transparent flexible sheet permeable to nutrients and oxygen before implantation into the subretinal space. Such a sheet will allow passage of biological nutrients and oxygen around the ISEMCPs. This sheet may also dissolve leaving behind ISEMCP units lying separately, or in an arranged pattern produced by a surrounding mesh. ISEMCPs may be of the PiN or NiP type or a combination of both in a single unit. An electric capacitor layer may also be incorporated into the ISEMCP device (ISEMCP-C) to allow charge storage during exposure to light and charge release in darkness producing an opposite polarity current. This last modification will allow the generation of hyperpolarizing currents in light and depolarizing currents in darkness which is necessary to produce formed vision of light and dark images.

39 Claims, 11 Drawing Sheets

OTHER PUBLICATIONS

Exhibit B is an article published in *Science*, Jul., 1981.

Granit R., Helme T. "Changes In Retinal Excitability Due To Polarization And Some Observations On The Relation Between The Processes in Retina And Nerve", *J. Neurophysiol*, 1939;; 2:556–565.

Knighton R. W. "An Electrically Evoked Slow Potential Of The Frog's Retina. I. Properties Of Response", *J. Neurophysiol*, 1975; 38–185–197.

Brindley, G. S. "The Site Of Electrical Excitation Of The Human Eye", *J. Physiol*, 1955; 127–189–200.

Brindley G. S., "Beats Produced By Simultaneous Stimulation Of The Human Eye With Intermittent Light And Intermittent Or Alternating Electric Current", *J. Physiol*, 1962; 164: 156–167.

Potts, A M, Inoue J., Buffum D., "The Electrically Evoked Response Of The Visual System (EER)", *Invest Ophthalmol Vis Sci.*, 1968; 7:269–278.

Humayun M. S., Propst R. H., Hickingbotham, D., deJuan E. Jr., Dagnelie G., "Visual Sensations Produced By Electrical Stimulation Of The Retinal Surface In Patients With End-Stage Retinitis Pigmentosa (RP)", ARVO Abstracts, *Invest Ophthalmol Vis. Sci.*, 1993; 34 (Suppl):835.

Tasman E., ed. *Duane's Foundations of Clinical Ophthalmology*, vol. 3, Philadelphia, Lippincott, 1992; chapter 13:20–25, chapter 60:1–12.

Stone J. L., Barlow, W. E., Humayun, M. S., deJuan E., Jr., Milam, A. H., "Morphometric Analysis Of Macular Photoreceptor And Ganglion Cells In Retinas With Retinitis Pigmentosa", *Arch Ophthalmol, 1992; 110:1634–1639.*

Pagon, R. A., "Retinitis Pigmentosa", *Surv Ophthalmol,.* 1988; 33:137–177.

Eagle, R. C., Lucier, A. C., Bernardino, V. B., et al., "Retinal Pigment Epithelial Abnormalities In Fundus Flavimaculatus", *Ophthalmol*, 1980; 87:1189–1200.

Hagins, W. A., Penn, R. D., Yoshikami, S. "Dark Current And Photocurrent In Retinal Rods", *Biophys J.*, 1970; 10:380–412.

Tomita, T., "Electrical Activity Of Vertebrate Photoreceptor", *Q Rev Biophys.*, 1970; 3:179–222.

Baylor, D. A., Fuortes, M. G. F., "Electrical Responses Of Single Cones In The Retina Of The Turtle", *J Physiol*, 1970; 207:77–92.

Chow, A. Y. "Electrical Stimulation Of The Rabbit Retina With Subretinal Electrodes And High Density Microphotodiode Array Implants", ARVO Abstracts, *Invest Ophthalmol Vis Sci.* 1993; 34 (Suppl):835.

Rubin, M. L., *Optics for Clinicians*, Gainsville, Traid Scientific Publishers, 1974; 119–123.

Boettner, E. A, Wolter, J. R. "Transmission Of The Ocular Media", *Invest Ophthalmol*, 1962; 1:776–783.

Shannon, R. V. "A Model Of Safe Levels For Electrical Stimulation", *IEEE Tarns Biomed Eng.*, 1992; 39:424–426.

Armington, J. C., Brigell, M. "Effects Of Stimulus Location And Pattern Upon The Visually Evoked Cortical Potential And The Electroretinogram", *Int J. Neurosci*, 1981; 14:169–178.

Fenwick, P. B. C., Stone, S. A. Bushman, J., Enderby, D., "Changes In The Patter Reversal Visual Evoked Potential As A Function Of Inspired Nitrous Oxide Concentration", *Electroencephalogr Clin Neurophysiol*, 1984; 57178–183.

Rovamo, J., Virsu, A., "An Estimation And Application Of The Human Cortical Magnification Factor", *Exp Brain Res.*, 1979; 37:495–510.

Dowling, J. E., Ripps, H, "Visual Adaptation In The Retina Of The Skate", *J Gen Physiol*, 1970; 56:491–520.

Humayun, M., Propst R., De Juan, E., et al. "Bipolar Surface Electrical Stimulation Of The Vertebrate Retina", *Arch Ophthalmol*, 1994; 112:110–116.

Narayanan, M. V., Rizzo, J. F., Edell, D., et al. "Development Of A Silicon Retinal Implant: Cortical Evoked Potentials Following Focal Stimulation Of The Rabbit Retina With Light And Electricity", ARVO Abstracts, *Invest Ophthalmol Vis Sci.*, 1994; 35(Suppl):1380.

Dawson, W. W., Radtke, N. D., "The Electrical Stimulation Of The Retina by Indwelling Electrodes", *Invest Ophthalmol Vis Sci.*, 1977; 16:249–252.

Brady, G. S., Clauser, H. R., *Materials Handbook, Thirteenth Edition*, New York, McGraw–Hill, 1991; 739–740.

Paton, D., Goldberg, M. F., *Management Of Ocular Injuries*, Philadelphia, W. B. Saunders Co., 1976; 134–135.

Terr, L. I., Linthicum, F. H., House, W. F., "Histopathologic Study Of The Cochlear Nuclei After 10 Years Of Electrical Stimulation Of The Human Cochlea", *Am J Otol.*, 1988,; 9:1–7.

Agnew, W. F. McCreery, D. B. *Neural Prostheses Fundamental Studies*, Englewood Cliffs, Prentice Hall, 1990; 25–65.

Curcio, C. A., Sloan, K. R., Kaliha, R. E. Hendrickson, A. E., "Human Photoreceptor Topography", *J of Comparative Neurology*, 1990; 292:497–523.

Brown, et al., "Monolithically Integrated 1 X 12 Array Of Planar InGaAs/InP Photodiodes", *Journal of Lightwave Technology*, vol. LT–4, No. 3, Mar. 1986, pp. 283–286.

Melen, et al. "A Transparent Electrode CCD Image Sensor For A Reading Aid For The Blind", *IEEE Journal Of Solid–State Circuits*, vol. SC–9, No. 2, Apr. 1974, pp. 41–48.

Kataoka, "An Attempt Towards An Artificial Retina: 3–D IC Technology For An Intelligent Image Sensor", *Transducers '85: International Conference On Solid–State Sensors And Actuators 1985*, pp. 440–442.

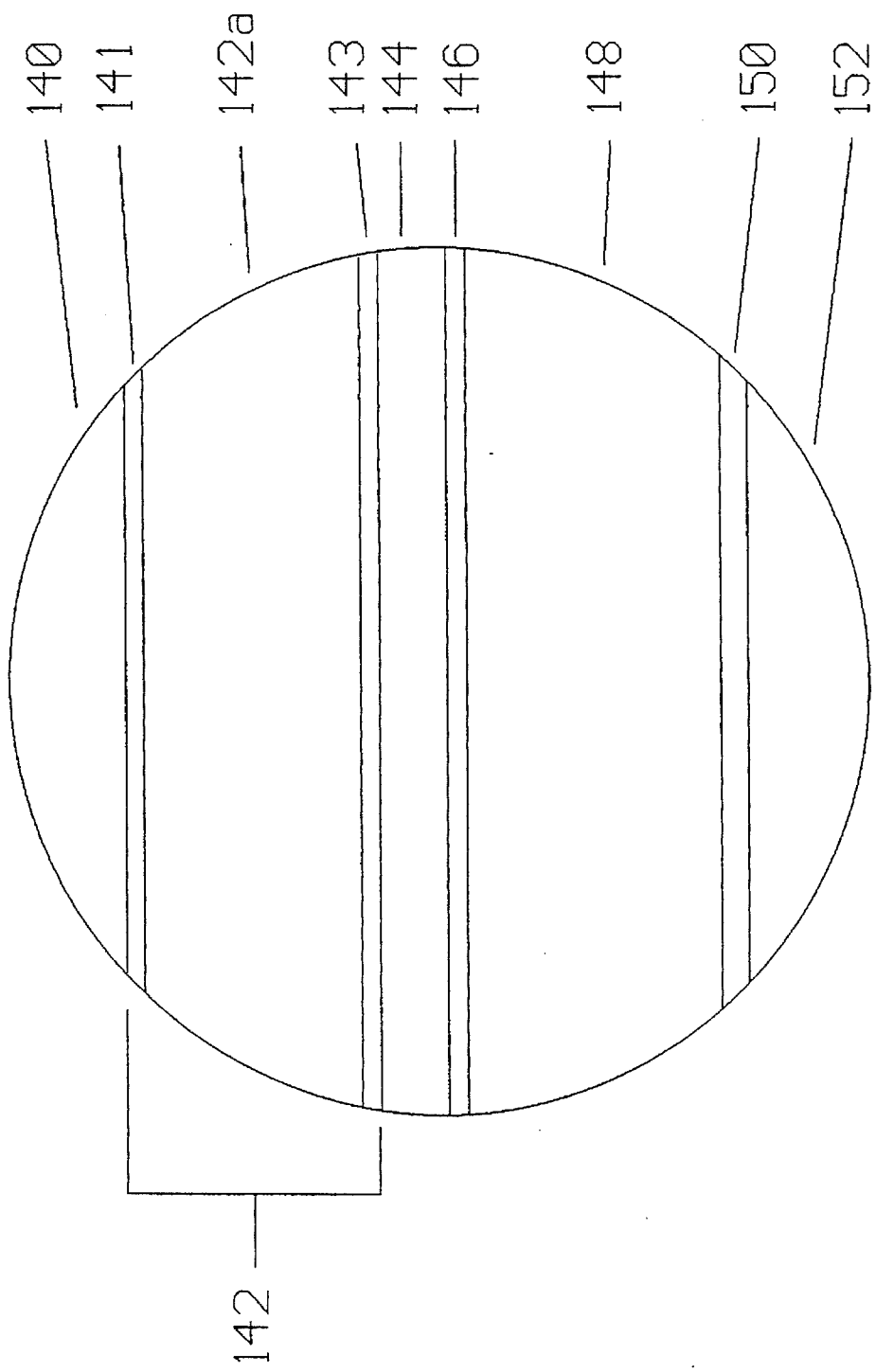

INDEPENDENT PHOTOELECTRIC ARTIFICIAL RETINA DEVICE AND METHOD OF USING SAME

This application is a continuation-in-part of U.S. patent application Ser. No. 08/056,672, filed May 3, 1993, issued as U. S. Pat. No 5,397,350, on Mar. 14, 1995.

BACKGROUND OF THE INVENTION

The present invention is a medical product that can be used to correct vision loss or even complete blindness caused by certain retinal diseases. A variety of retinal diseases cause vision loss or blindness by destruction of the vascular layers of the eye including the choroid and choriocapillaris, and the outer retinal layers including Bruch's membrane and retinal pigment epithelium. Loss of these layers is followed by degeneration of the outer portion of the inner retina beginning with the photoreceptor layer. Variable sparing of the remaining inner retina composed of the outer nuclear, outer plexiform, inner nuclear, inner plexiform, ganglion cell and nerve fiber layers, may occur.

Prior efforts to produce vision by stimulating various portions of the retina have been reported. One such attempt involved an externally powered photo-sensitive device with its photoactive surface and electrode surfaces on opposite sides. The device theoretically would stimulate the nerve fiber layer via direct placement upon this layer from the vitreous body. The success of this device is unlikely due to it having to duplicate the complex frequency modulate neural signals of the nerve fiber layer. Furthermore, the nerve fiber layer runs in a general radial course with many layers of overlapping fibers from different portions of the retina. Selection of appropriate nerve fibers to stimulate to produce formed vision would be extremely difficult, if not impossible.

Another prior device involved a unit consisting of a supporting base onto which a photosensitive material such as selenium is coated. This device was designed to be inserted through an external scleral incision made at the posterior pole. It would rest between the sclera and choroid or between the choroid and retina. Light would cause a potential to develop on the photosensitive surface producing ions which would then theoretically migrate into the retina causing stimulation. However, having no discrete surface structure to restrict the directional flow of charges, lateral migration and diffusion of charges would occur thereby preventing any resolution capability. Placement of this device between the sclera and choroid would also result in blockage of discrete ion migration to the photoreceptor and inner retinal layers. This is due to the presence of the choroid, choriocapillaris, Bruch's membrane and the retinal pigment epithelial layer all of which would block passage of these ions. Placement of the device between the choroid and the retina would still interpose Bruch's membrane and the retinal pigment epithelial layer in the pathway of discrete ion migration. As this device would be inserted into or through the highly vascular choroid of the posterior pole, subchoroidal, intraretinal and intraorbital hemorrhage would likely result along with disruption of blood flow to the posterior pole. One such device was reportedly constructed and implanted into a patient's eye resulting in light perception but no formed imagery.

The present inventor reported a design for a subretinally placed photovoltaic device comprised of multiple surface electrode microphotodiodes (SEMCPs) deposited on a single silicon crystal substrate. These SEMCPs transduce light passing through a semitransparent electrode surface onto the photoactive surface into small electric currents which stimulate overlying and surrounding inner retinal cells. Due to the solid nature of the substrate onto which the SEMCPs were placed, blockage of nutrients from the choroid to the inner retina occurs. Even with fenestrations of various geometries, permeation of oxygen and biological substances is not optimal.

SUMMARY OF THE INVENTION

The artificial retina device of this invention is composed of multiple independent surface electrode microphotodiodes (ISEMCP") within a liquid or other suitable vehicle designed to be injected into the subretina space of the eye. Each ISEMCP is a discrete P-i-N or N-i-P semiconductor of a size typically smaller than 1000 microns.

When a plurality of such ISEMPCs are inserted subretinally into the space between the inner and outer retinal layers, each device produces an amplitude-modulated electric current when incident light passes through its semitransparent front electrode surface. The amplitude of this current varies directly with the intensity of illumination of the ISEMCP. Thus, each ISEMCP will depolarize and/or hyperpolarize a small area of the overlying inner retinal layer, which consists of photoreceptors, bipolar cells and horizontal cells. As these cells in normal eyes would both receive and produce analog amplitude-modulated currents, the similarly modulated output of the ISEMCPs in a dysfunctional eye with outer retinal layer damage would likewise stimulate these cells.

Alignment of the ISEMCPs in the subretinal space may be random in which case only those ISEMCPs with favorable alignment towards incident light will produce electric current. However in one embodiment of this invention, alignment may be directed by application of an external magnetic field upon the ISEMCPs which will have an incorporated off-centered ferromagnetic layer. Alternatively, ISEMCPs may also be embedded in a transparent flexible substance for implantation into the subretinal space. This substance may be fabricated from nondissolvable hydrophilic and nutrient-permeable substances such as used to fashion soft contact lenses, for example, a hydrophilic polymer of poly (2-hyroxyethylmethacrylate); or it may be made from dissolvable substances such as agar or collagen. A fine mesh made of an inert substance such as nylon or polypropylene may also surround the individual ISEMCPs producing a patterned arrangement of the subunits.

In another embodiment, each ISEMCP can include an electrical capacitor layer, so that the modified unit (hereafter "ISEMCP-C") will be able to produce opposite direction electrical currents in light and darkness to induce the visual sensations of light and darkness upon the retina.

BRIEF DESCRIPTION OF THE DRAWINGS

FIG. 11 is a side view of a single ISEMCP-C microsphere unit showing its microarchitecture, including an off-centered ferromagnetic layer at one pole.

DETAILED DESCRIPTION OF THE PRESENTLY PREFERRED EMBODIMENTS

Figure 1:
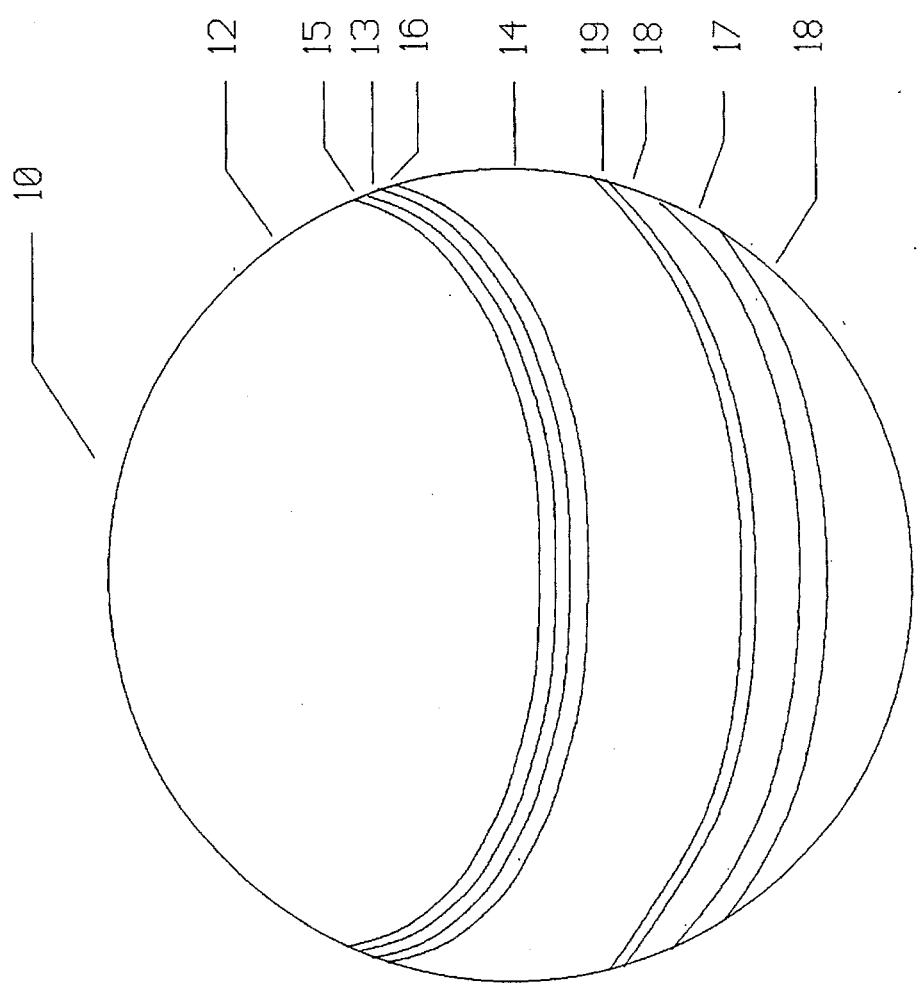
FIG. 1 is a perspective view of a single ISEMCP microsphere unit showing its layered microarchitecture.

As illustrated in FIG. 1, the surface microarchitecture of one presently preferred embodiment of the photoelectric device of the invention is generally designated at 10. In the preferred embodiment, such photoelectric device comprises a P-i-N-type ISEMCP discussed above, although those skilled in the art will appreciate that other photoelectric devices can be employed without departing from the spirit and scope of the invention. As shown in FIG. 1, the preferred ISEMCP 10 forms a spherical shape and is sized in microscopic dimensions.

In its basic form, the P-i-N ISEMCP 10 contains a semitransparent surface electrode 12. The surface electrode 12 is preferably made of polysilicon created by standard ion implantation, thermal diffusion or chemical vapor deposition techniques. Alternatively, the surface electrode 12 may be constructed of any suitable material that will conduct electric current and allow light to pass through it. Thus, the surface electrode 12 may also be made of a thin, semitransparent layer of gold, which has been vacuum deposited over a thin semitransparent layer of chromium. (Chromium is used to improve adhesion of the gold layer to the other layers described below.) Other conductive materials which can be used instead of gold include aluminum and platinum.

As shown in FIG. 1, the surface electrode 12 forms the positive electrode of a semiconductor photodiode, which is formed at the P junction 13 between the surface electrode 12 and a negatively doped substrate 14. Between the surface electrode 12 and the junction 13 is an enhanced polysilicon (P+) layer 15, which allows good electrical contact between the electrode and the junction 13. The P junction 13 also contacts one side of an intrinsic (i) layer 16, which occurs naturally in the manufacture of the microphotodiode. On the opposite side of the intrinsic layer 16 is the negatively doped bulk silicon substrate 14.

The P junction 13 and the negatively doped substrate 14, therefore, form the P-N halves of the semiconductor photodiode included in each ISEMCP 10. Behind the doped substrate layer 14, are additional layers, including an optional layer of magnetically susceptible material 17 (described below), negatively doped polysilicon layers 18, and an enhanced conductive $N^+$ layer 19 where the doped substrate 14 contacts the negative polysilicon (N) layer 18.

In the preferred embodiment of the invention, the diameter of an ISEMCP is between 1 to 25 microns. However, in alternate embodiments, the ISEMCP may be manufactured as small as 0.1 micron or as large as 1000 microns diameter without departing from the spirit and scope of the invention. An ISEMCP with a diameter smaller than 15 microns will have to be manufactured to have a rod-like structure to allow the depth needed to incorporate all the necessary layers. Similarly, in the preferred embodiment, each ISEMCP has a high ohmic (resistive) value with resistances between 1 ohm/cm and 50,000 ohm/cm. As those skilled in the art will also appreciate, the above-described, preferred ISEMCP 10 has been shown in a P-i-N configuration of semitransparent surface electrodes, but an N-i-P silicon microphotodiode may also be readily manufactured and is thus equivalent to the preferred ISEMCP 10.

Figure 2:
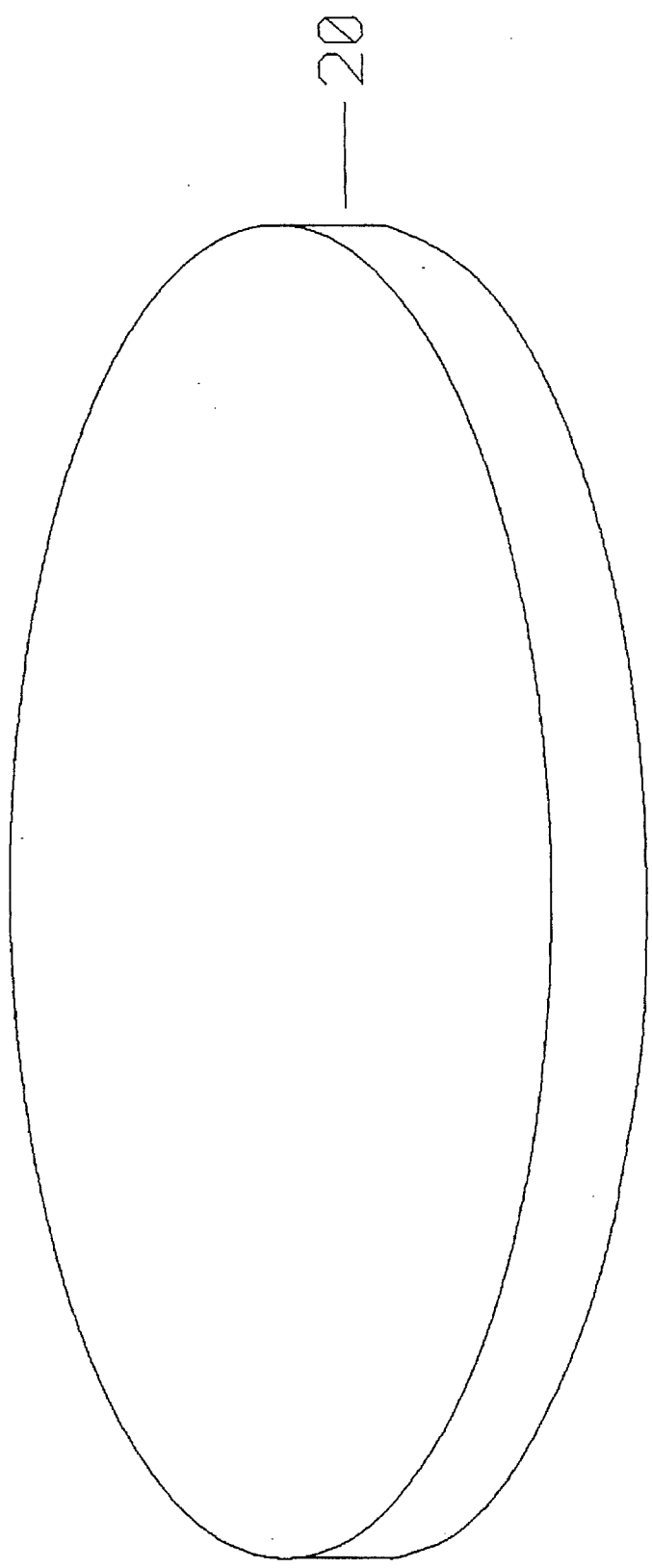
FIG. 2 is a perspective view of a silicon wafer used in the manufacture of the preferred ISEMCP's of the invention.
Figure 3:
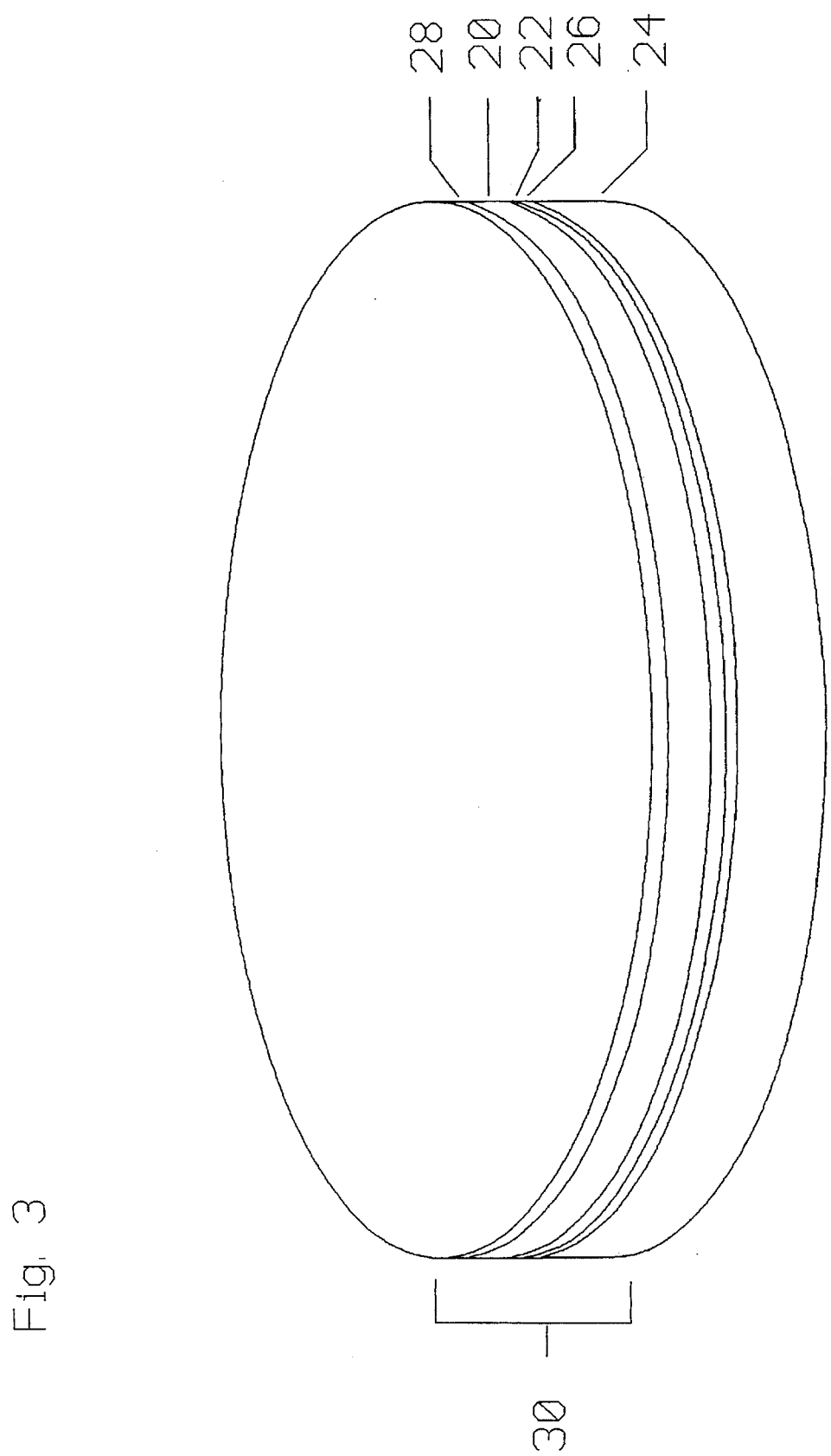
FIG. 3 is a perspective view of the materials added to the silicon wafer of FIG. 2 in the manufacture of the ISEMCP's.
Figure 4:
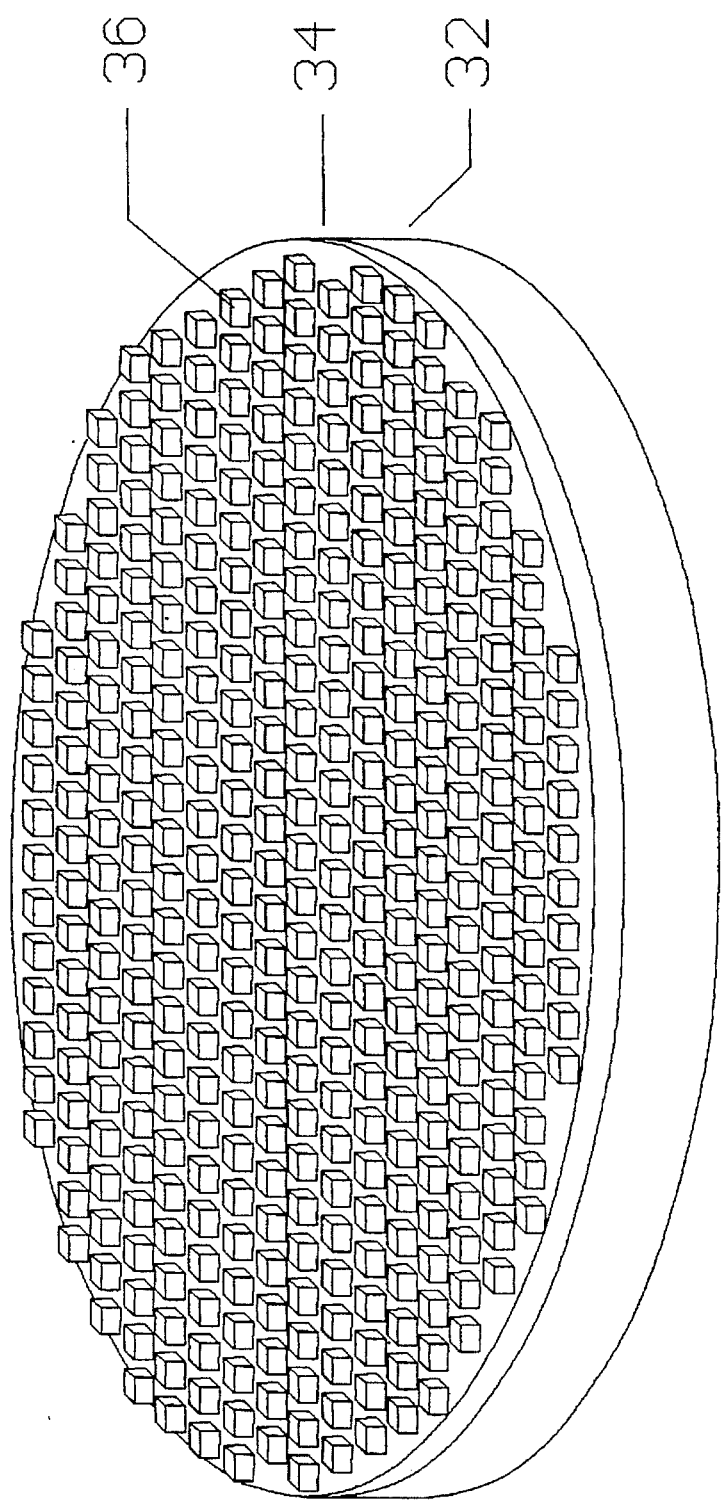
FIG. 4 is a perspective view of plural ISEMCP microcubes prior to lapping.

A typical manufacturing process for the preferred P-i-N ISEMCP 10 microsphere shown in FIG. 1, having dimensions of approximately 25 microns, is shown in FIGS. 2–4. As shown in FIG. 2, the first stage in the manufacture of such ISEMCP's includes mechanically lapping a basic three inch diameter N-doped silicon wafer 20 from a typical manufactured thickness of 21 mils to an ultra-thin starting thickness of five mils. This preferred starting thickness allows sufficient mechanical strength for further processing, which is described below. By starting with a thin wafer, moreover, the complexity of these subsequent steps is substantially reduced.

With standard ion implantation, thermal diffusion or chemical vapor deposition techniques, the bottom surface of the wafer 20 is converted into a single region P-junction semiconductor, as shown in FIG. 3. Preferably, seven microns of P-doped polysilicon is added to the wafer 20 as the P anode, which forms part of the P layers 22. The P layers 22 include layers 12, 13 and 15 of the preferred ISEMCP shown in FIG. 1. The P layers 22 also include the intrinsic layer 16, which is created after P junction 13 ion implantation.

The bottom side of the wafer 20 (the P-doped polysilicon side) is then affixed to a ceramic disk 24 with a chemically soluble non-aqueous adhesive 26. As those skilled in the art will appreciate, this technique is similar to that used in mirror grinding and failure analysis cross-sectioning. With the increased mechanical strength afforded by the ceramic disk 24, the topside of the wafer 20 is again lapped mechanically to a thickness of two mils. At this stage of the manufacturing process it is also preferable to ensure that the front and back surfaces of the wafer 20 are parallel. Final thinning of the silicon wafer 20 is accomplished by standard chemical etch. A target thickness of 11 microns for the non-polysilicon portion is thus achieved.

A shallow $N^+$ layer 28 is then implanted on the top of the negatively doped substrate 20. The $N^+$ layer is deposited using standard ion implantation techniques generally known in the art. Next, a seven micron N-doped polysilicon layer is laid down, which serves as the N cathode electrode 18 shown in FIG. 1. The N-doped polysilicon layer is deposited using chemical vapor deposition techniques, also generally known to those skilled in the art.

When complete, the final structure is preferably 25 microns thick: seven microns of P poly 22, 11 microns of silicon bulk 20, and seven microns N poly 28 (with the intrinsic layer 16 (FIG. 1) being formed between the P-poly 22 and the bulk 20 layers).

The final wafer assembly 30 is then laser sliced along the X direction to produce strips of silicon 25 microns wide. Because of the small dimensions of the cut, excimer laser slicing is preferred. Lateral damage into the silicon by the excimer laser is less than one micron. The assembly 30 is then laminated onto a second ceramic disk 32 (similar to the first piece) whose function is to hold all silicon slices in place when the wafer is again laser cut in the Y direction. Unlike the adhesive 26 of FIG. 3, the aqueous adhesive 34 used in this step is preferably not dissolvable in the solvent used in the next step. Thus, the assembly 30 is placed in a nonaqueous solvent that dissolves the first adhesive, but not the second.

The assembly 30 is laser cut along the Y direction with the same pitch as previously employed in the X direction. When completed, the wafer 20 will have been converted into a plurality of microcubes 36 (FIG. 4), each of which is 25 microns on a side. The assembly 30 is finally placed into a second aqueous solvent to dissolve the remaining adhesive 34. When the second adhesive layer 34 is dissolved, the silicon microbes 36 remain suspended in the solvent. The bulk ceramic disk base 32 is then removed from the solution, leaving only the suspended silicon microcubes 36. The silicon microcubes 36 are then recovered and placed in a water suspension. As those skilled in the art will realize, the fabrication of N-i-P devices is similar to the above process except with the reversal of the P and N stages.

Depending on the desired shape of the ISEMCP's chosen, a certain amount of polishing is then performed on the silicon microcubes 36. To polish the silicon microcubes 36, the water suspension of microcubes 36 is placed between two circular glass lapping plates (not shown) in a manner generally known in the art. These plates are capacitively monitored and time/pressure controlled to provide a very precise polishing action. With this approach, the cubic silicon structures 36 are polished into smooth silicon microspheres 10 (shown in FIG. 1) with precise and consistent diameters. When lapping is completed, the silicon ISEMCP microspheres 10 are washed, recovered, sterilized and placed in a physiologically compatible semi-solid or liquid vehicle ready for injection or implantation into the eye.

Referring again to FIG. 1, because the P region 13 governs the active junction depletion zone where photon conversion occurs, only microspheres with the P surface electrode 12 facing incident light will respond by producing a photoelectric current. The designed and preferred electric current output of each ISEMCP 10 is on the order of one to 5,000 nA depending on ambient lighting. Nevertheless, a range of 0.01 nA to 20,000 nA is also suitable. The ISEMCP's 10 may also be modified to achieve a greater or smaller output, depending upon the stimulation requirements of the overlying cell layer, by changing the size of the ISEMCP's 10 and/or the thickness of the semitransparent surface electrodes 12 and 18. As the amplitude of the output of each ISEMCP 10 is modulated by the intensity of the incident light, its effect on the inner retina and bipolar cells will be similar to the photoreceptors at this initial site. It may also preserve the on-off receptor fields function providing contrast recognition in addition to producing formed images.

Figure 5:
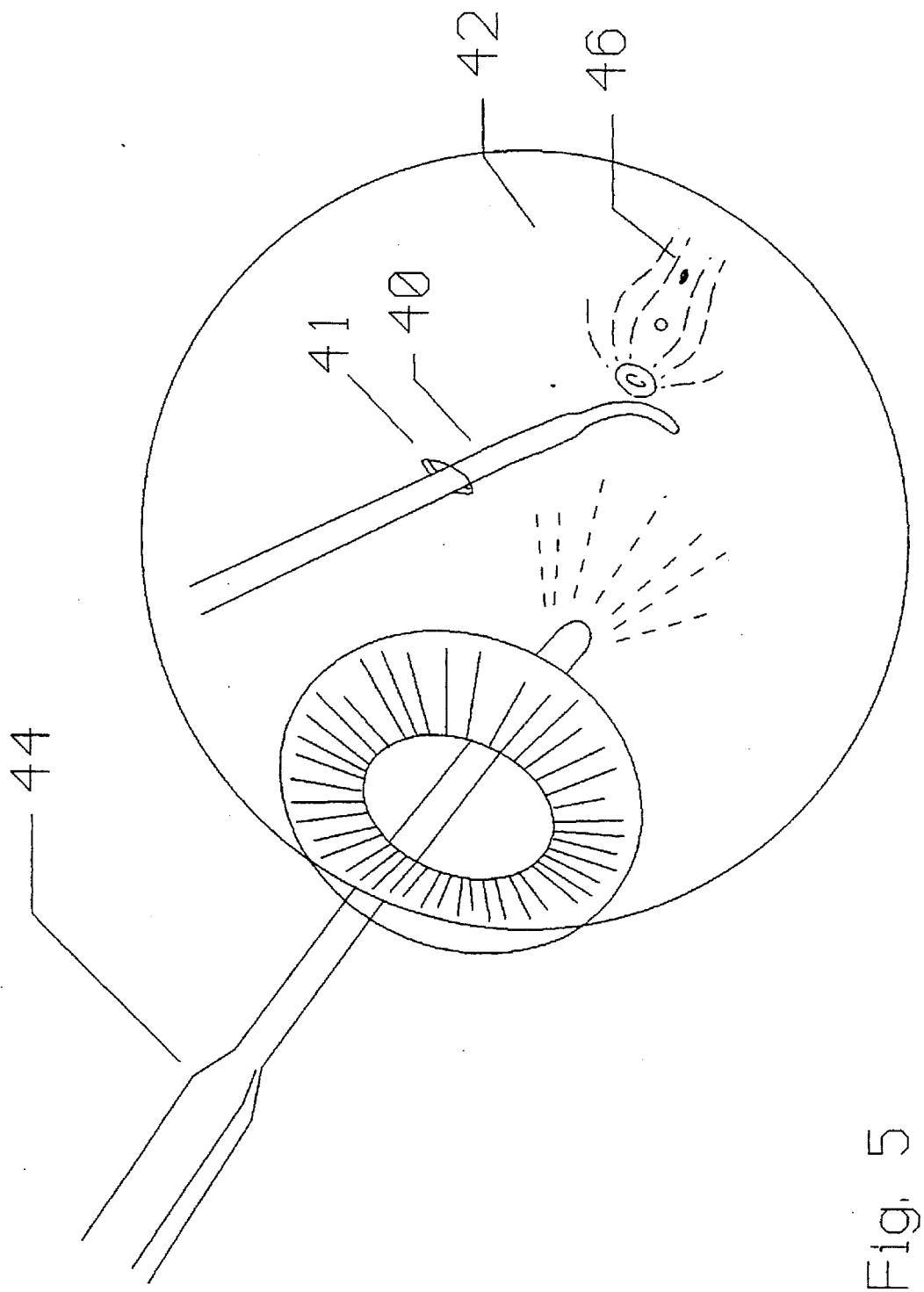
FIG. 5 illustrates a canula being inserted into the subretinal space ready for subretinal injection and implantation of the ISEMCP's.

As illustrated in FIG. 5, the photoelectric device of this invention is preferably implanted into the subretinal space by injection with a very fine canula 40. Preferably, the ISEMCP's are placed in a vehicle such as (but not limited to) a liquid, and injected into the subretinal space via a retinotomy incision 46 using the canula 40. Such a liquid vehicle may be a balanced salt solution or a more viscous material like methylcellulose. A viscous vehicle will allow more even suspension of the ISEMCP's than the balanced salt solution. Other vehicles include oxygen- and nutrient-permeable semi-solid solutions.

The retina 42 is preferably illuminated by a light pipe 44 to facilitate the injection of the ISEMCP's. As shown in FIG. 5, the canula 40 is introduced into the vitreous cavity of the eye via a pars plana incision 41. Dissection of the posterior vitreous is performed to separate the posterior hyaloid face from the retinal surface. A small retinotomy incision 46 is made through the retina following the direction of the nerve fiber layer using a stiletto type MVR blade. Dissection of the inner retina from the outer retinal layers is accomplished mechanically with the canula 40.

Figure 6:
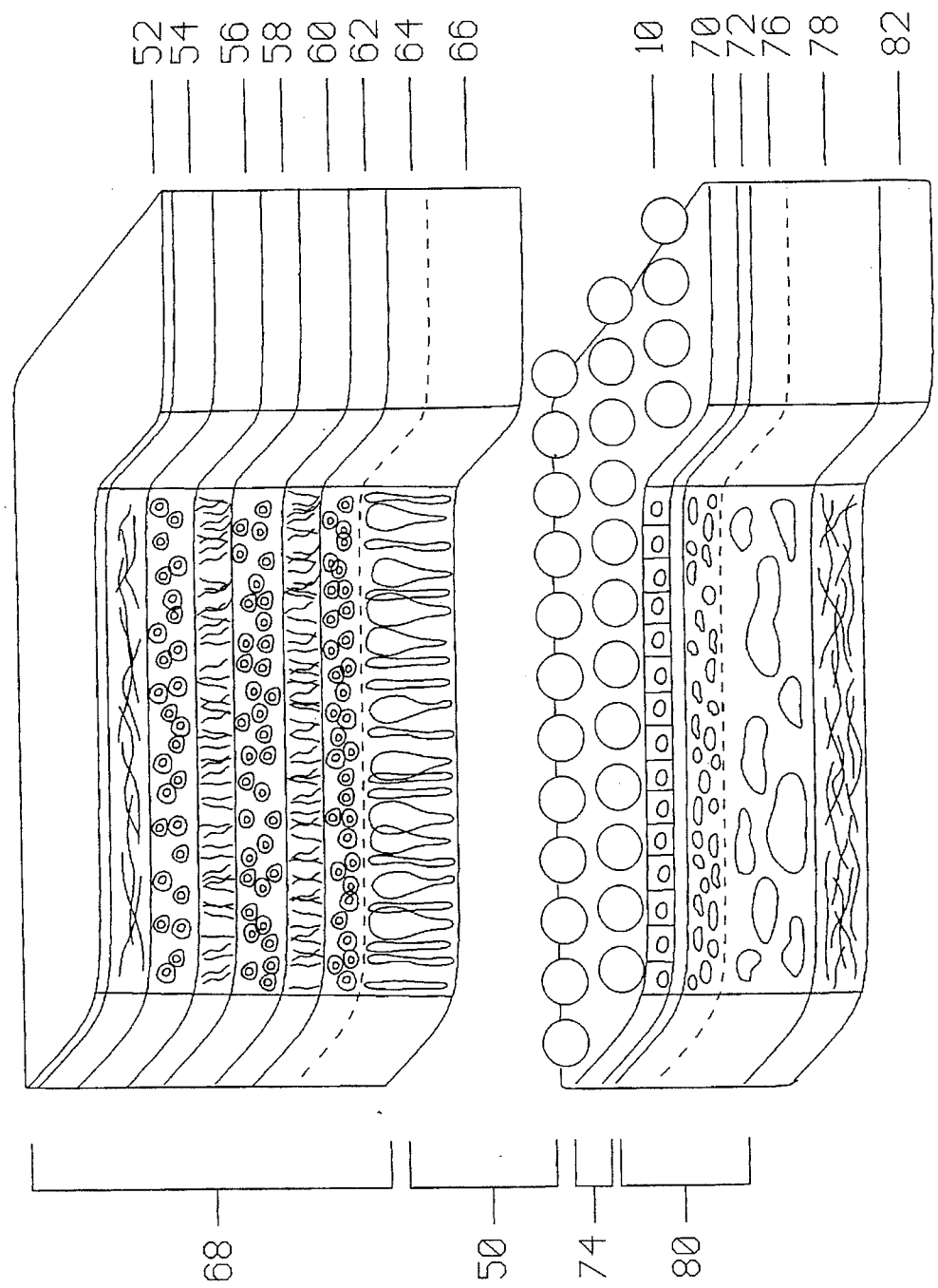
FIG. 6 is an exploded cross-sectional view of a portion of the retina illustrating plural ISEMCP's in their preferred location in the subretinal space between the inner and outer retinal layers.

When the appropriate retinal areas to receive the implantation have been prepared with canula dissection, the liquid vehicle with suspended ISEMCP's is injected. An attempt should be made to distribute the suspended ISEMCP's 10 in a uniform monolayer, as shown in FIG. 6. The canula 40 is then withdrawn and a heavier-than-water non-miscible material (preferably, a perfluorocarbon) is optionally placed over the posterior pole of the vitreous cavity to aid in settling of the retina. The non-miscible material is preferably removed after an appropriate time, usually 15 to 20 minutes, leaving a reattached retina. With settling and reattachment of the retina, the implanted ISEMCP's 10 will tend to become distributed into the desired monolayer.

In FIG. 6, the ISEMCP's 10 are shown in their preferred monolayer position in the subretinal space 50. The layers of the eye at the posterior pole from inside to outside are also shown in FIG. 6 in their respective positions: internal limiting membrane 52; nerve fiber layer 54; ganglion and amacrine cell layer 56; inner plexiform 58; inner nuclear layer 60; outer plexiform 62; outer nuclear and bipolar cell layer 64; and photoreceptor layer 66, all of which constitute the inner retinal layer 68. The ISEMCP's 10 are thus disposed between the inner retinal layer 68, and retinal pigment epithelium 70 and Bruch's membrane 72, which constitute the outer retinal layer 74. External to the outer retina, choriocapillaris 76 and choroid 78 comprise the choroidal vasculature 80 and sclera 82, the outer coat of the eye.

Figure 7:
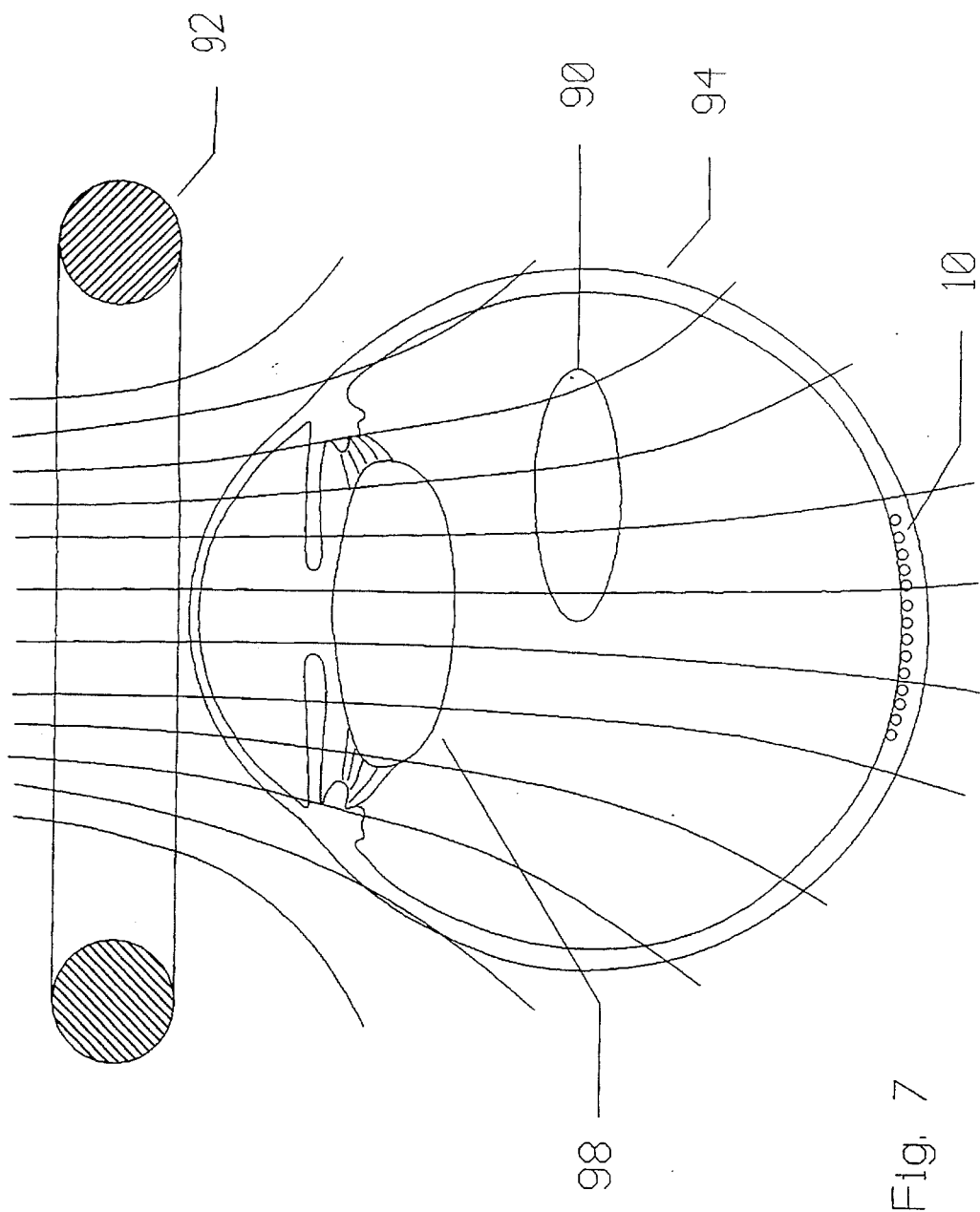
FIG. 7 illustrates a magnetic field produced by an electromagnetic coil placed at the occiput area of the head directing alignment of ISEMCP's or ISEMCP-Cs implanted in the subretinal space.

As illustrated in FIG. 7, the ISEMCP's 10 may be aligned after insertion by use of a magnetic field 90 produced by an electromagnetic coil 92 or the like placed in the vicinity of the eye 94. As many of the ISEMCP's 10 as possible should be oriented so that the P-doped layer 15 (FIG. 1) is oriented to receive incident light through the lens 98 of the eye 94 (FIG. 7). Magnetic field lines 90 shown in FIG. 7 will interact with the dipole characteristics of the ISEMCP's 10 and produce appropriate alignment of the majority of the ISEMCP's 10, similar to the behavior of iron filings near a magnet. The ISEMCP's 10 have innate dipole characteristics when photo-stimulated, so magnetic orientation should be performed while the ISEMCP's 10 are illuminated. Alternatively, the ISEMCP's 10 can be embedded with substances (preferably, nickel, nickel alloy, cobalt, samarium, palladium, or magnetically susceptible ceramics) that have strong magnetic susceptibility (FIG. 1) to assist in obtaining such beneficial alignment. As shown in FIG. 1, these magnetically susceptible substances 17 are preferably disposed within the N polysilicon electrode on the rear of the ISEMCP's 10. In manufacture, these substances are deposited partway into the N polysilicon deposition phase, and are preferably vacuum deposited. The magnetically susceptible material may also be deposited external to the N-polysilicon electrode in the most posterior position of the device.

Figure 8:
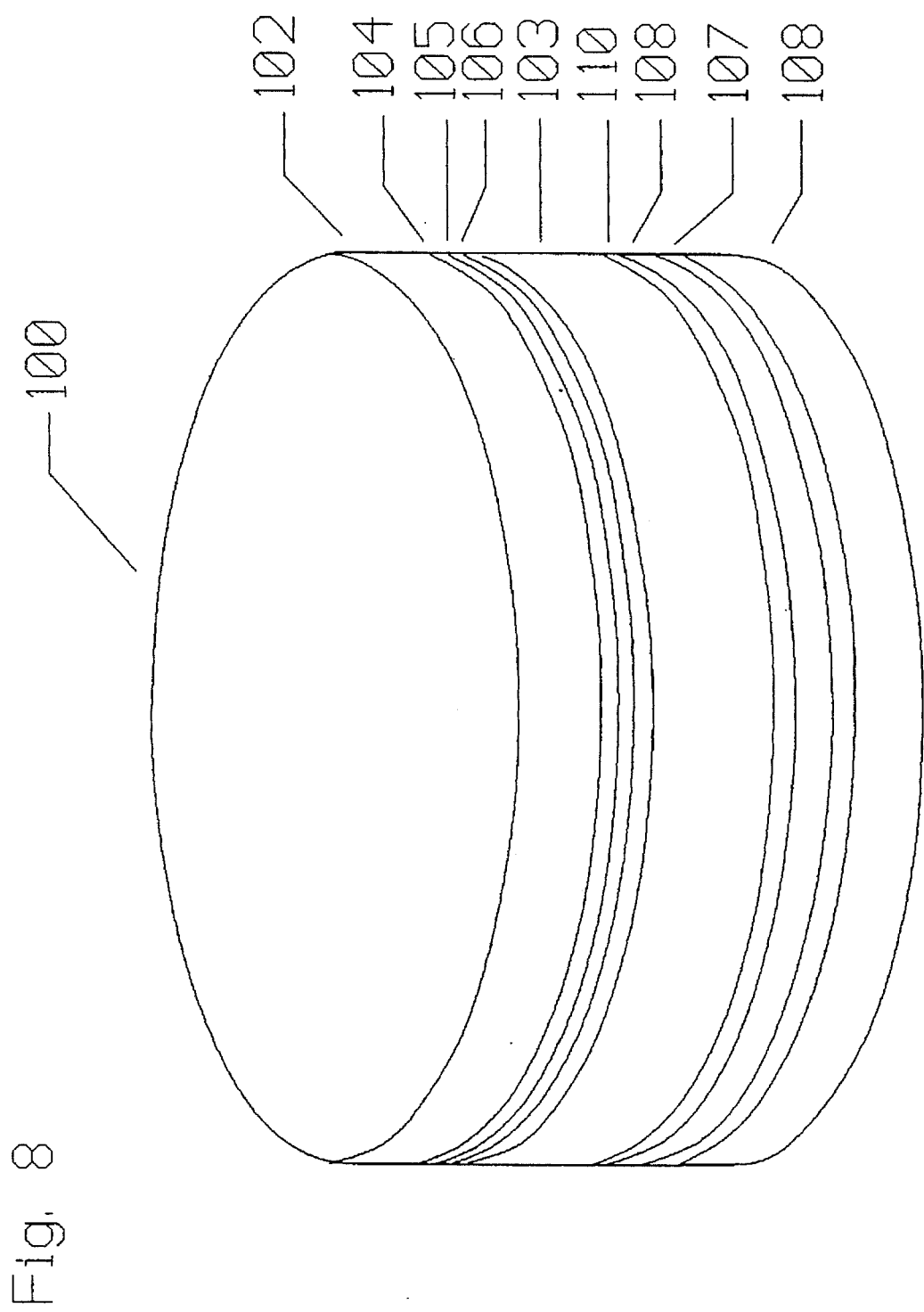
FIG. 8 is a perspective view of a single ISEMCP microdisc unit showing the layered architecture shown in FIG. 1.

As mentioned above, the ISEMCP's may take on other microscopic structures without departing from the spirit and essential scope of the invention. For example, as shown in FIG. 8, another embodiment of the ISEMCP 100 may be as a microcylinder structure with semitransparent surface electrodes 102 and 108, P$^+$ layer 104, P junction layer 105, intrinsic layer 106, N substrate layer 103, N$^+$ layer 110, N-polysilicon layer 108 and magnetically susceptible material layer 107. The microdisc ISEMCP's 100 shown in FIG. 8 are preferably manufactured to diameters on the order of 0.5 micron to 2000 microns. These units are fabricated similarly to the microspheres shown and described above in connection with FIG. 1, with the exception that their larger size results from a larger original dicing specification. Additionally, the microcylinder ISEMCP's 100 are lapped a shorter time than the microsphere ISEMCP 10 units in order to preserve their cylindrical shape, but sufficient to round the corners of the microcubes to a smooth circular finish.

Figure 9:
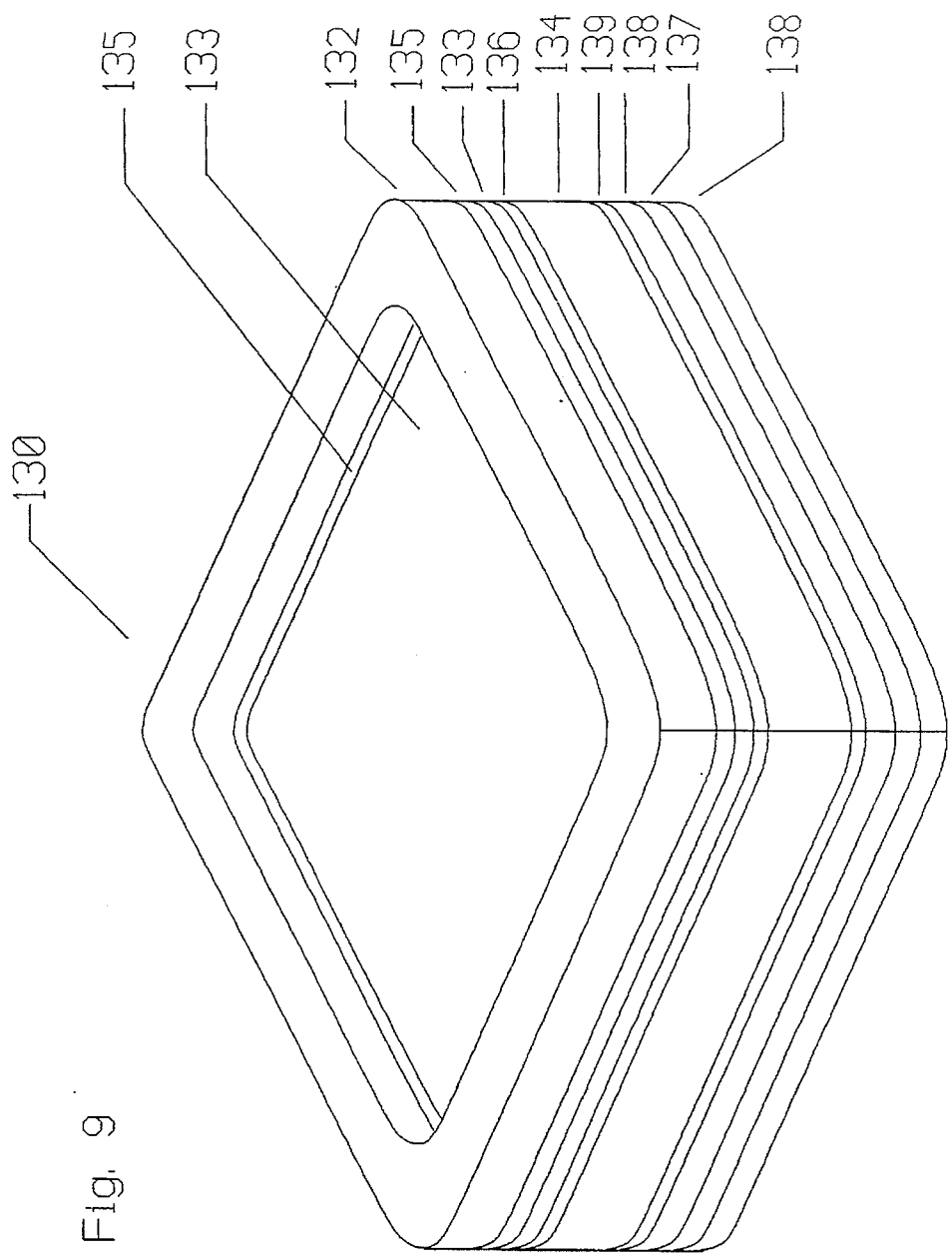
FIG. 9 is also a perspective view of an ISEMCP microdisc where the front surface electrode covers only a fraction of the photo-active surface.

Alternatively, another embodiment of the ISEMCP devices of the invention is shown in FIG. 9. In this embodiment, the semitransparent surface electrode 132 of this photoelectric device covers only a fraction of the photo-active surface of the device 130. As shown in FIG. 9, the surface electrode 132 is disposed along the periphery of the ISEMCP 130, but as those skilled in the art will appreciate, the surface electrode 132 may take on other shapes covering a fraction of the photo-active surface. The photoelectric device of FIG. 9 otherwise resembles the devices discussed above in most other respects. As shown in FIG. 9, this device includes a P$^+$ layer 135, P junction layer 133, intrinsic layer 136, N substrate layer 134, N$^+$ layer 139, N-polysilicon layer 138, magnetically susceptible material layer 137, and posterior semitransparent surface electrode 138.

The advantage of covering a fraction of the photo-active surface, such as with the elevated rim electrode 132 shown in FIG. 9, of course, is that electrode material is eliminated from in front of the photo-active surface. Attenuation of light may still be accomplished, however, by controlling the thickness of the P junction 133. A further advantage of the embodiment shown in FIG. 9 is that less lapping is required. Only enough lapping to produce the rounded edges is needed.

Figure 10:
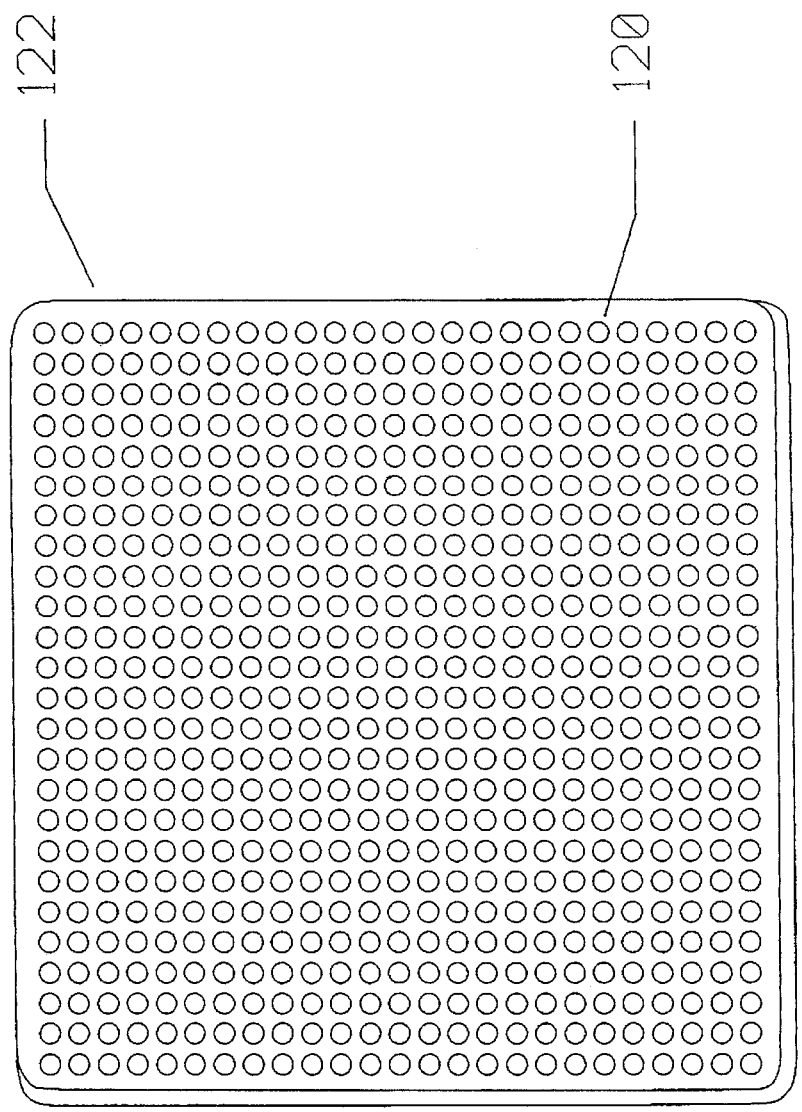
FIG. 10 is a plan view of plural ISEMCP subunits embedded in a substrate of oxygen- and nutrient-permeable, non-dissolvable or dissolvable, material.

Although the preferred method for insertion of the ISEMCP's described above involves injection of ISEMCP's suspended in a balanced salt or viscous solution, alternate forms of implantation are contemplated. For example, as shown in FIG. 10, individual ISEMCP's 120 may be embedded in a substrate sheet 122 and pre-aligned by use of a magnetic field. This sheet 122 may be cut to the dimensions of the area of retinal dysfunction by a surgeon, and implanted subretinally through a similar retinotomy incision as shown for the microsphere ISEMCP's in FIG. 5. The sheet 122 is preferably made of nutrient- and oxygen-permeable material, such as (but not limited to) the common materials used to fashion soft contact lenses. Such a substance could be, for example, a hydrophilic polymer of poly (2-hyroxyethylmethacrylate). An embedded two-dimensional mesh made of an inert material, such as nylon or polypropylene, may also be used to provide even separation of the ISEMCP subunits 120.

Alternatively, the ISEMCP's 120 may also be placed in a dissolvable material, such as (but not limited to) agar and collagen. Implantation of agar or collagen sheets 122, with embedded pre-aligned ISEMCP's 120, into the subretinal space would allow even separation of individual ISEMCP's 120 pre-aligned toward the incident light.

A N-i-P ISEMCP-C is shown in FIG. 11. The microarchitecture of each N-i-P ISEMCP-C in its preferred embodiment consists of a front semitransparent N polysilicon layer which is the front surface electrode 140, followed by a P silicon bulk layer 142. Layer 142 is the N-i-P portion of the N-i-P ISEMCP-C and consists of a front surface layer 141 created by ion implantation with N-type phosphorous, and a rear surface layer 143 created by ion implantation with P-type boron. Formed between layers 141 and 143 is the intrinsic layer 142a. Progressing rearward, additional layers of the N-i-P ISEMCP-C are; a P-polysilicon electrode layer 144, a SiO$_2$ dielectric capacitor layer 146, another P-polysilicon electrode layer 148, a SiO$_2$ insulating layer 150, and a ferromagnetic nickel or nickel alloy layer 152. Layers 140–144 comprise the N-i-P microphotodiode, and layers 144–148 comprise an integrated series capacitor. Layer 144 is a common electrode layer shared by the N-i-P microphotodiode and the integrated series capacitor.

The purpose of the integrated series capacitor built into each photodiode microsphere structure is to store charge during "light vision" and release charge during "dark vision". "Light vision" occurs when bright images are focused onto the N-i-P surface, e.g. a star or a bright sky. "Dark vision" occurs when dark details are focused onto the N-i-P surface, e.g. the dark letters forming words on a printed page, or shadows. Normal vision comprises constantly changing "light" and "dark" vision as details of varying brightness and darkness intensities transfer across the retina. Vision with the ISEMCP-C involves the same type of transition across the N-i-P surfaces of the plural microphotodiodes in the eye. In "light vision" negative ions concentrate around the area of layer 140 produced by the N-i-P microphotodiode. This produces hyperpolarization of the overlying retina cells similar to their response to light if the cells were healthy photoreceptors in a normal eye. For dark images, the integrated series capacitor releases charges of opposite polarity (positive charges) via layer 144 which would be attracted in the direction of layer 140. This allows depolarization of the overlying retina cells also similar to their response to dark images if the cells were healthy photoreceptors in a normal eye. In addition to light and dark detail perception, the reversal of charge polarities in light and darkness in the overlying retina is important in maintaining the health of this layer. A constant and large accumulation of charges of one polarity may cause cellular damage from electrolysis activity. The ISEMCP-C allows for reversal of charge polarities and prevents accumulation of charges of one polarity.

The N-i-P microphotodiode structure, 140–144 on the light facing top portion of the microsphere serves as an electric current source for both stimulating the retina and charging the integrated series capacitor in "light vision." During "light vision", the N-i-P structure will produce several nanoamps of current directly correlating with the light intensity of the image focused on the microsphere. This current will flow into surrounding interstitial tissues from layer 144 and return into the N-i-P structure via layer 140. At the same time, another current loop charges the integrated series capacitor 144–148. This second current loop originates from the N-i-P structure from layer 144, progresses through layers 146 and 148, then into the interstitial cellular environment and reenters the N-i-P structure at layer 140. During "dark vision", current from the N-i-P structure decreases and current from the integrated series capacitor 144–148 flows from layer 144 into the interstitial cellular environment and completes the circuit upon reentering layer 148.

The P side of the N-i-P portion of the microsphere is coupled to the anode of the integrated series capacitor via a 2 micron thick P-doped boron polysilicon electrode 144. A thin layer of 0.2 micron silicon dioxide 146, serves as the dielectric layer of the capacitor. The cathode connection is also P-doped boron polysilicon 148. The 2 micron thick polysilicon anode electrode 144, has a bulk resistance of around 17 ohms while its lateral sheet resistance is around 40 K-ohms. The microcapacitor has a value of about 0.2 pF or 200 femtofarads.

During "light vision", current from the N-i-P photodiode charges the integrated series capacitor almost instantaneously since the RC time constant is in subnanoseconds. During "dark vision," a reduction or absence of photodiode current will occur. In this state, the integrated series capacitor will bleed current back into the surrounding interstitial tissues through the rim of the anode capacitor electrode 144. The time constant of this process is much longer than the charging RC time constant but is still in submicroseconds. Relative to the vision process, both charge and discharge time constants have ample response speeds to produce vision.

The typical fabrication of 30 micron diameter N-i-P ISEMCP-C microspheres of the type illustrated in FIG. 11 starts with a basic 3" 400 ohm-cm P type silicon wafer that is 21 mils thick. The wafer is ion implanted to 0.5 microns depth with N-type phosphorous on the front surface becoming layer 141 in the final N-i-P ISEMCP-C microsphere. This wafer will hereafter be referred to as the "target wafer". Using chemical vapor deposition (CVD), six (6) microns of phosphorous doped polysilicon at 10 ohm-cm is deposited onto the front surface of the target wafer becoming eventually layer 140 in the N-i-P ISEMCP-C microsphere.

A dummy 3" wafer is then oxidized with 4 microns thickness of $SiO_2$. Using normal photoresist and masking techniques, this oxide layer is patterned and etched to leave behind an X-Y grid. The width of the ribs in the grid are 254 microns wide (10 mils). The open area within each grid cell measures 3,600×3,600 microns square. This special dummy wafer will later be oxide bonded to the target wafer to restore the mechanical strength needed for further wafer thinning.

The dummy wafer is then laser drilled with an IR laser at the center of each square grid with a 125 micron (5 mils) diameter through hole. These holes serve two purposes. They will aid in the wafer oxide bonding step described below, and serve as the reflow hole for the glue used during final chip dicing.

The target wafer is mechanically lapped down on the P-bulk silicon side to a thickness of 178 microns (7 mils). The target wafer is then oxide bonded to the dummy wafer prepared above. Specifically, the front side (phosphorous N-doped polysilicon side) of the target wafer (140) is bonded to the oxide layer of the dummy wafer.

The target wafer is again mechanically lapped down to a thickness of 25 to 50 microns (1 to 2 mils). During lapping, the wafer assembly is affixed to the grinding head using the dummy wafer.

Final target wafer thinning is then accomplished using standard silicon chemical etch to a final thickness of 10 microns ±20% (0.31 to 0.47 mils). At this point, the target wafer is 16 microns (6 microns of polysilicon and 10 microns of silicon bulk).

For the next step, ion implantation is used to drive 0.5 microns of boron (P dopant) 143, into the P-silicon bulk 142 exposed backside of the target wafer. This serves as the interface to the next polysilicon deposition step. Two microns of 10 ohm-cm P+ boron-doped polysilicon 144 is then deposited using chemical vapor deposition. This layer of polysilicon 144 forms the positive electrode of the integrated series microcapacitor (144–148).

A layer of 0.2 micron silicon dioxide is deposited on the target wafer forming 146, the dielectric of the integrated series capacitor. Next, a thick layer of 8.3 microns P+ boron-doped polysilicon 148 is deposited. The resistivity of this layer is about 10 ohm-cm and forms the negative electrode of the microcapacitor. The finished microcapacitor (144–148) will have a capacitance of about 200 femtofarads.

A layer of 0.5 micron silicon dioxide 150 is deposited which serves as an insulator between the layers 148 and 152. This insulating layer is necessary to prevent current flow through the next layer which may cause electrical dissolution of the layer. The final layer is an E-beam deposited nickel or nickel alloy coating 152 of 9 microns thickness. The ferromagnetic property of the nickel or nickel alloy will impart magnetic susceptibility to the sphere in the presence of a magnetic field. This will allow in-situ alignment of the micro-spheres in the subretinal space after surgical implantation, using a magnetic field described above.

The total structure thickness is now 36 microns; 6 microns N-Poly 140, 10 microns P silicon bulk 142 with embedded N-i-P layers 141, 142a, and 143, 2 microns P-Poly 144, 0.2 microns $SiO_2$ 146, 8.3 microns P-Poly 148, 0.5 micron $SiO_2$ 150, and 9 microns nickel or nickel alloy 152. This wafer assembly is now reflowed through the holes in the dummy wafer with an optical balsam glue. The glue will fill and harden within the cavity of each grid cell in preparation for dicing.

An IR or excimer laser is used to dice along the X and Y directions to produce silicon squares 36 microns on a side. Lateral laser damage into silicon is less than 1 micron. Since the wafer thickness is also 36 microns, the end result is many 36 micron per side active silicon cubes held in place by the optical balsam. Any residual energy from the laser beam is absorbed by the balsam and dummy wafer.

The wafer assembly is placed into a liquid solvent upside down to dissolve the balsam glue. All micro-cubes then separate away from the wafer assembly and settle to the bottom of the glass container. The dummy wafer assembly is now discarded. Washing and rinsing is completed using traditional techniques. After the silicon microspheres are cleaned and dried, they are ready for abrasive shaping.

The silicon micro-cubes are placed into a centrifugal polisher using deionized water as the carrier solution. The walls of the polisher are smooth Pyrex glass. Under a combination of tumbling and swirling, the micro-cubes will abrasively ride the surface of the glass wall and slowly lap into spheres. This process takes approximately one to two weeks, depending on the polisher parameters.

When lapping is completed, the silicon microspheres, now 30 microns in diameter, are cleaned, rinsed, dried and recovered. The micro-spheres are sterilized and suspended in saline or a viscous fluid ready for implantation into the eye.

As can be seen, the photoelectric artificial retina device of this invention provides significant advantages over the prior art. The preferred ISEMCPs allow oxygen and nutrients to flow readily between the outer and inner retinal layers. Further, the individual microscopic geometries of these devices allows for accurate implantation into irregular areas of outer retinal dysfunction. Such implantation can be achieved by either injecting the ISEMCPs which are suspended in a physiologically compatible liquid or semi-solid vehicle, or by direct implantation of ISEMCP impregnated permeable materials. Because the complex conversion of amplitude-modulated signals to frequency-modulated signals is left to intrinsic retinal mechanisms, formed vision with subretinally implanted ISEMCP's is greater than with devices that attempt to stimulate the nerve fiber layer directly.

It is to be understood that a wide range of changes and modification to the embodiments described above will be apparent to those skilled in the art, and are also contemplated. It is therefore intended that the foregoing detailed description be regarded as illustrative rather than limiting, and that it be understood that it is the following claims, including all equivalents, that are intended to define the spirit and scope of the invention.

We claim:

1. A method of producing artificially formed vision in an eye, comprising the step of introducing a plurality of discrete microscopic photoelectric devices into the subretinal space of the eye wherein at least some of said photoelectric devices include a capacitative storage element that produces opposite direction electrical currents in light and darkness, permitting formed vision of light and dark images as a result of light and dark images received by the retina.

2. The method defined in claim 1, wherein said plurality of discrete microscopic photoelectric devices are introduced as discrete microphotodiodes.

3. The method defined in claim 2, wherein said plurality of discrete microphotodiodes are introduced as P-i-N semiconductors.

4. The method defined in claim 2, wherein said plurality of discrete microphotodiodes are introduced as N-i-P semiconductors.

5. The method defined in claim 2, further comprising the steps of suspending the plurality of microphotodiodes in a liquid, and injecting the resulting suspension into the subretinal space.

6. The method defined in claim 5, wherein the plurality of microphotodiodes are introduced by a canula for implantation into the subretinal space.

7. The method defined in claim 6, wherein the plurality of microphotodiodes are introduced into the vitreous cavity by creation of a pars plana incision.

8. The method defined in claim 7, wherein the posterior vitreous is dissected to separate the posterior hyaloid face from the retinal surface, and an incision is made through the retina and into the subretinal space.

9. The method defined in claim 8, wherein the subretinal space is entered with a small retinotomy incision along the direction of the nerve fiber layer, followed by dissection of the inner retina from the outer retina.

10. The method defined in claim 5, wherein the liquid comprises a balanced salt solution.

11. The method defined in claim 5, wherein the liquid comprises a viscous agent.

12. The method defined in claim 11, wherein the viscous agent comprises methylcellulose.

13. The method defined in claim 5, further comprising the steps of injecting a liquid that is non-miscible in water over the posterior pole in the vitreous cavity of the eye after the suspension is injected to aid in the settling of the retina, and then removing the non-miscible liquid after the retina is settled.

14. The method defined in claim 13, wherein the non-miscible liquid comprises perfluorocarbon.

15. The method defined in claim 13, wherein the non-miscible liquid is removed an appropriate time period after it has been injected.

16. The method defined in claim 1, further comprising the step of aligning the microphotodiodes to receive light incident upon the eye.

17. The method defined in claim 16, wherein the microphotodiodes are aligned with a magnetic field.

18. A light powered artificial subretinal implant device comprising a carrier vehicle and a plurality of discrete photoelectric devices, wherein each photoelectric device comprises a photo-active surface and a corresponding first electrode disposed on the photoelectric device, a second electrode disposed on the photoelectric device spaced from the first electrode, and a capacitive storage element disposed on the photoelectric device and electrically connected to the second electrode to store electric charge generated by the photoelectric device in light conditions and to release electric charge in dark conditions to permit formed vision of light and dark images.

19. The artificial subretinal implant device defined in claim 18, wherein the plurality of discrete photoelectric devices comprise discrete independent surface electrode microphotodiodes.

20. The artificial subretinal implant device defined in claim 19, wherein the independent surface electrode microphotodiodes comprise P-i-N semiconductors.

21. The artificial subretinal implant device defined in claim 19, wherein the independent surface electrode microphotodiodes comprise N-i-P semiconductors.

22. The artificial subretinal implant device defined in claim 19, wherein the first electrode is semitransparent.

23. The artificial subretinal implant device defined in claim 19, wherein the first electrode conducts electric current and allows passage of light through it.

24. The artificial subretinal implant device defined in claim 19, wherein the first electrode is fabricated from the group consisting of polysilicon, gold, chromium, iridium, aluminum and platinum.

25. The artificial subretinal implant device defined in claim 19, wherein the first electrode covers a fraction of the photo-active surface of the microphotodiodes.

26. The artificial subretinal implant device defined in claim 19, wherein the microphotodiodes comprise a substantially spherical shape.

27. The artificial subretinal implant device defined in claim 19, wherein the microphotodiodes comprise a cylindrical or rod-like shape.

28. The artificial subretinal implant device defined in claim 19, further comprising a magnetically susceptible layer, in each photoelectric device wherein the magnetically susceptible layer facilitates alignment of the microphotodiodes in the subretinal space by application of an external magnetic field and comprises a substance from the group consisting of palladium, tungsten, cobalt, nickel, nickel alloy, iron, iron alloy, samarium, and magnetically susceptible ceramics.

29. The artificial subretinal implant device defined in claim 19, wherein the carrier vehicle comprises a liquid.

30. The artificial subretinal implant device defined in claim 19, wherein the carrier vehicle comprises a viscous material.

31. The artificial subretinal implant device defined in claim 19, wherein said carrier vehicle comprises a sheet of oxygen and nutrient permeable material, wherein the plurality of discrete photoelectric devices are embedded in the sheet, and wherein the discrete devices are placed in the sheet and pre-aligned to incident light.

32. The artificial retinal implant device defined in claim 31, wherein the sheet of oxygen and nutrient permeable material comprises a non-dissolvable material.

33. The artificial retinal implant device defined in claim 32, wherein the non-dissolvable material comprises a hydrophilic polymer of poly (2-hyroxyethylmethacrylate).

34. The artificial retinal implant device defined in claim 31, wherein the sheet of oxygen and nutrient permeable material comprises a dissolvable material.

35. The artificial retinal implant device defined in claim 34, wherein the dissolvable material comprises agar.

36. The artificial retinal implant device defined in claim 34, wherein the dissolvable material comprises collagen.

37. The artificial retinal implant device defined in claim 19, wherein individual microphotodiodes are embedded in a mesh-like network made of an inert substance.

38. The artificial retinal implant device defined in claim 37, wherein the mesh-like network comprises nylon.

39. The artificial retinal implant device defined in claim 37, wherein the mesh-like network comprises polypropylene.

* * * * *

UNITED STATES PATENT AND TRADEMARK OFFICE
CERTIFICATE OF CORRECTION

PATENT NO. : 5,556,423
DATED : September 17, 1996
INVENTOR(S) : Alan Y. Chow et al.

It is certified that error appears in the above-indentified patent and that said Letters Patent is hereby corrected as shown below:

In the Claims

In claim 32, line 1, delete "retinal" and substitute --subretinal--.

In claim 33, line 1, delete "retinal" and substitute --subretinal--.

In claim 34, line 1, delete "retinal" and substitute --subretinal--.

In claim 35, line 1, delete "retinal" and substitute --subretinal--.

In claim 36, line 1, delete "retinal" and substitute --subretinal--.

In claim 37, line 1, delete "retinal" and substitute --subretinal--.

In claim 38, line 1, delete "retinal" and substitute --subretinal--.

UNITED STATES PATENT AND TRADEMARK OFFICE
CERTIFICATE OF CORRECTION

PATENT NO.   : 5,556,423
DATED        : September 17, 1996
INVENTOR(S)  : Alan Y. Chow et al.

It is certified that error appears in the above-indentified patent and that said Letters Patent is hereby corrected as shown below:

In claim 39, line 1, delete "retinal" and substitute --subretinal--.

Signed and Sealed this

Sixteenth Day of September, 1997

Attest:

BRUCE LEHMAN

Attesting Officer

Commissioner of Patents and Trademarks